United States Patent
Wood et al.

(10) Patent No.: US 8,709,102 B2
(45) Date of Patent: Apr. 29, 2014

(54) DYEING COMPOSITION FOR KERATIN FIBERS

(75) Inventors: Jonathan Wood, Weinheim (DE); Anja Aechtner, Mannheim (DE); Axel Blake, Mühltal (DE)

(73) Assignee: KAO Germany GmbH, Darmstadt (DE)

( * ) Notice: Subject to any disclaimer, the term of this patent is extended or adjusted under 35 U.S.C. 154(b) by 0 days.

(21) Appl. No.: 13/993,549

(22) PCT Filed: Dec. 23, 2011

(86) PCT No.: PCT/EP2011/073944
§ 371 (c)(1),
(2), (4) Date: Jun. 12, 2013

(87) PCT Pub. No.: WO2012/089663
PCT Pub. Date: Jul. 5, 2012

(65) Prior Publication Data
US 2013/0255008 A1   Oct. 3, 2013

(30) Foreign Application Priority Data
Dec. 27, 2010 (EP) .................................. 10016085

(51) Int. Cl.
| A61Q 5/10 | (2006.01) |
| C09B 1/16 | (2006.01) |
| A61K 8/22 | (2006.01) |
| A61K 8/35 | (2006.01) |
| C09B 1/20 | (2006.01) |
| C09B 69/00 | (2006.01) |

(52) U.S. Cl.
CPC ... *A61Q 5/10* (2013.01); *A61K 8/22* (2013.01); *A61K 8/355* (2013.01); *C09B 1/207* (2013.01); *C09B 69/00* (2013.01); *A61K 2800/882* (2013.01)
USPC .................. 8/405; 8/406; 8/426; 552/237

(58) Field of Classification Search
CPC ........................................... A61Q 5/10
USPC .................... 8/405, 406, 643, 657, 675, 426; 552/237
See application file for complete search history.

(56) References Cited

U.S. PATENT DOCUMENTS

2009/0217466 A1*   9/2009   Barbieru et al. .................. 8/407

FOREIGN PATENT DOCUMENTS

EP         1 820 826 A1    8/2007

OTHER PUBLICATIONS

STIC Search Report dated Jul. 24, 2013.*
International Search Report mailed Apr. 12, 2012.

* cited by examiner

*Primary Examiner* — Eisa Elhilo
(74) *Attorney, Agent, or Firm* — Norris McLaughlin & Marcus, P.A.

(57) ABSTRACT

Present invention relates to dyeing composition for keratin fibers especially human hair comprising cationic anthrachinone dye. The first object of the present invention is a dyeing composition for keratin fibers especially human hair resulting from mixing of two parts A and B wherein part A has an alkaline pH and comprises at least one cationic antraquinone dye and at least one additional dyestuff selected from direct and oxidative dyes and part B has an acidic pH and comprises at least one oxidizing agent.

18 Claims, No Drawings

DYEING COMPOSITION FOR KERATIN FIBERS

This application is a 371 application of PCT/EP2011/073944 filed Dec. 23, 2011, which claims foreign priority benefit under 35 U.S.C. §119 of European Application No. 10016085.2 filed Dec. 27, 2010.

Present invention relates to dyeing composition for keratin fibers especially human hair comprising cationic anthrachinone dye.

Keratin fibers dyeing has been carried out with compositions comprising oxidative dyes as well as direct dyes. The disadvantageous of dyeing keratin fibers with direct dyes are mainly that the colors achieved are not long lasting, they are sensitive to the environmental effects, do not dye hair homogeneously. These drawbacks haven been addressed in many patent documents. These disadvantages have been partly solved for some types of the dyestuffs but remained unsolved for blue dyes and therefore colors comprising blue dyestuffs still need to be optimized. Additionally colors obtained lack vibrancy, especially in the parts having varying degree of damage. It is especially important for people wearing colored hair that initial color characteristics are kept as long as possible.

Present invention starts from the above problems and aims at providing compositions for dyeing keratin fibers especially human hair for achieving long lasting, homogeneous colors which look excellently and homogeneously vibrant on hair having various degree of damage.

The inventors of the present invention has surprisingly found out that a dyeing composition for keratin fibres resulting from mixing of two parts A and B wherein part A has an alkaline pH and comprises at least one cationic antraquinone dye and at least one additional dyestuff selected from direct and oxidative dyes and part B has an acidic pH and comprises at least one oxidizing agent colours hair excellently homogeneous and the colours so obtained are long lasting on keratin fibers, especially human hair, and especially they are best suited for achieving violet colors or more generally achieving colour shades which requires a blue dyestuff and colours are excellently vibrant with long lasting vibrancy especially on keratin fibers especially human hair having various degree of damage in its length.

The blue dyestuffs have been known form the patent publication WO 2007/090799 A2. The said document lists various types of dyes and discloses their suitability for dyeing hair but does not disclose any hair dyeing compositions comprising additional dyestuff and especially does not address the problem of improved and long lasting vibrancy together with achieving homogeneous vibrancy on keratin fibers having various degree of damage in its length.

Accordingly, the first object of the present invention is a dyeing composition for keratin fibres especially human hair resulting from mixing of two parts, A and B, wherein part A has an alkaline pH and comprises at least one cationic antraquinone dye selected from

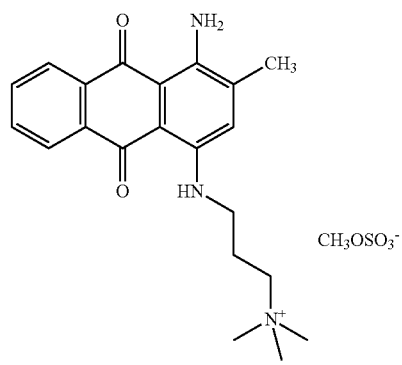

(Ia)

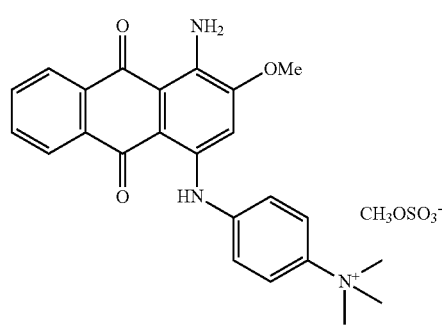

(Ib)

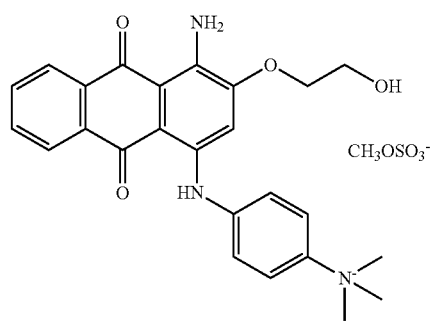

(Id)

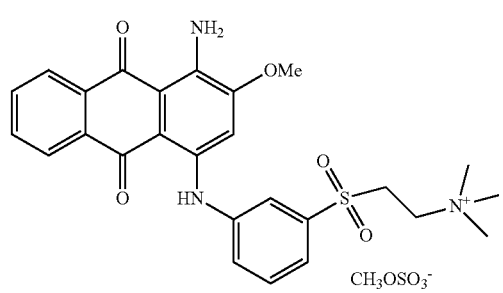

(Ie)

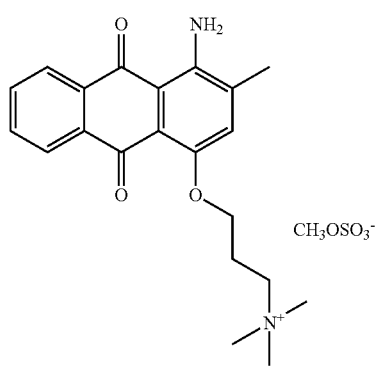
(If)
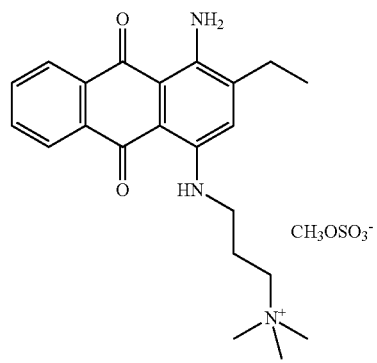
(Is)
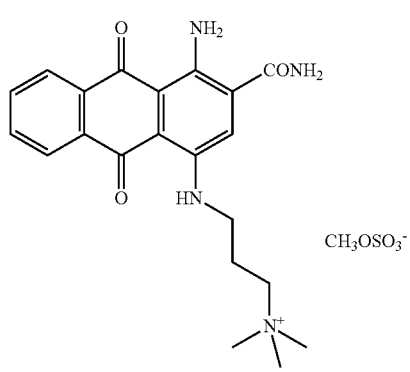
(Ig)
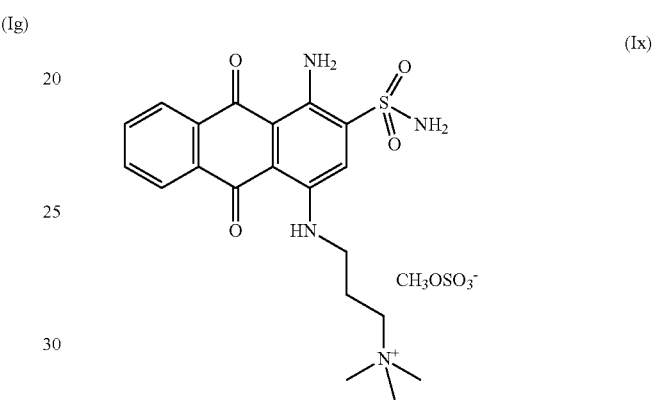
(Ix)
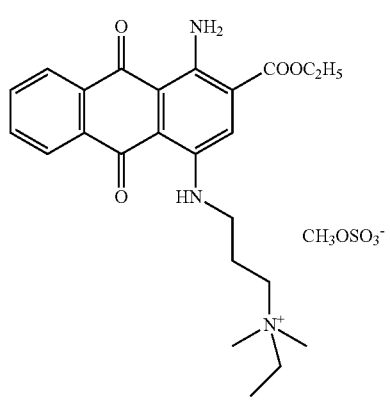
(Ih)
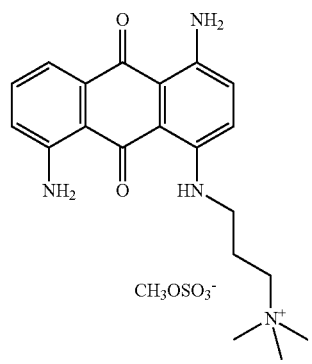
(Ij)
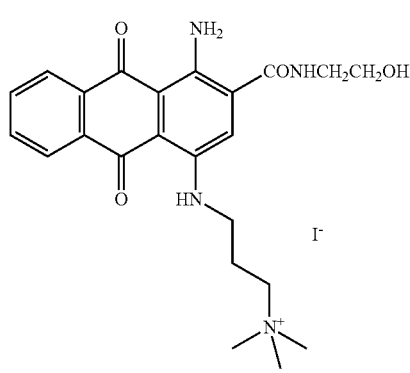
(Ir)
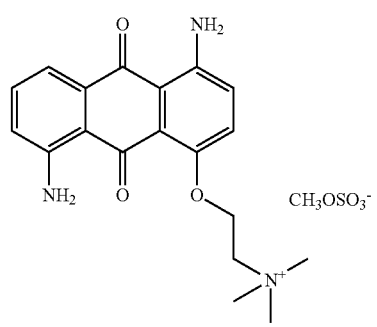
(Ik)

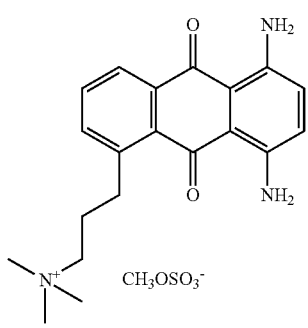
(Il)
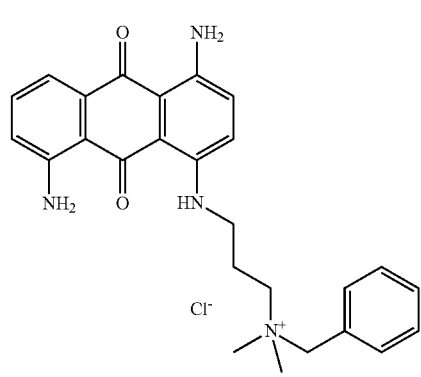
(Iu)
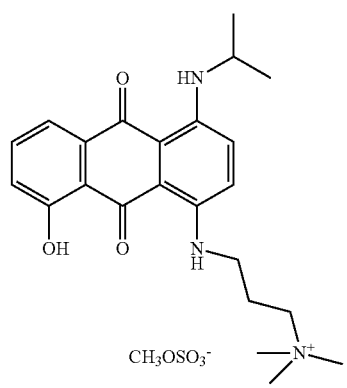
(Im)
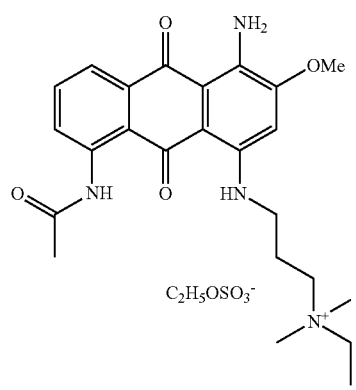
(Iy)
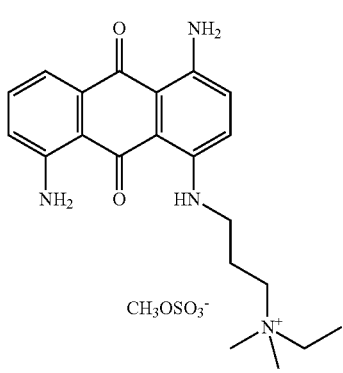
(In)
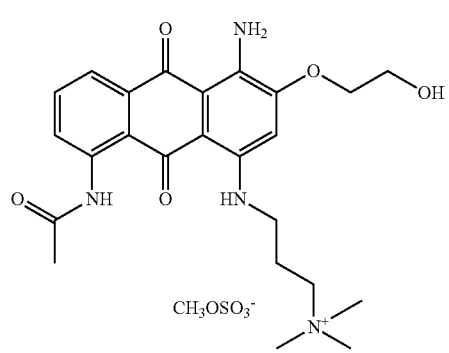
(Iv)
(It)
(Iw)

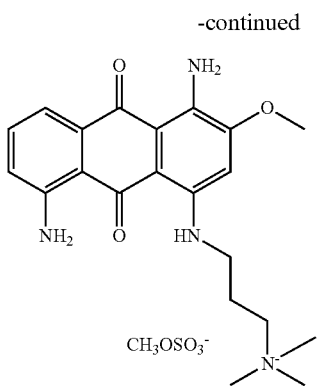

(Iz)

and at least one additional dyestuff selected from direct and oxidative dyes and part B has an acidic pH and comprises at least one oxidizing agent.

Second object of the present invention is the use of the composition for dyeing keratin fibers, especially human hair, especially for achieving long lasting homogeneous vibrant blue comprising colors.

Third object of the present invention is process for coloring keratin fibers especially human hair wherein a composition according to the present invention is applied onto hair and processed 1 to 45 min and rinsed off from hair and hair is optionally treated with another composition and optionally rinsed off and optionally dried.

Part A comprises at least one antraquinone dyestuff selected from the ones given above. The most preferred dyestuff is the one according to structure 1a given above.

Part A of the composition comprises at least one antroquinone dyestuff at a concentration of 0.0001 to 10%, preferably 0.001 to 7.5%, more preferably 0.01 to 5% and most preferably 0.01 to 3% by weight calculated to total composition, prior to mixing with the part B.

Additional hair dye is selected from oxidative dye precursors and direct dyes. Suitable direct dyes are selected from cationic dyes, anionic dyes and neutral nitro dyes.

Part A comprises at least one oxidative dye precursor as an additional hair dye. Some examples are p-phenylenediamine, p-methylaminophenol and substituted p-phenylenediamines such as 2,5-diamino-toluene, 2-n-propyl or 2-ethyl-p-phenylenediamine, 2,6-di-methyl-p-phenylenediamine, 2-(2,5-diaminophenyl)ethanol, 1-amino-4-bis-(2'-hydroxy-ethyl) amino-benzene, 2-(2-hydroxyethyl amino)-5-aminotoluene, 4,4'-diaminodiphenylamine, 4-aminodiphenylamine, 2-amino-5-N,N-diethyl aminotoluene, 4-amino-N-ethyl-N-isopropyl aniline, 2-chloro-p-phenylenediamine, 1-β-hydroxyethyl-2,5-diamino-4-chlorobenzene, 1-β-hydroxyethyl-2,5-diamino-4-methyl benzene, 2-methoxy-p-phenylenediamine, N,N-diethyl-p-phenylenediamine, 1-amino-4-β-methoxyethyl aminobenzene, 1-dimethylamino-4-aminobenzene, 1-hydroxy-2,5-diamino-4-methyl benzene, 1-hydroxymethyl-2,5-diaminobenzene, 1,3-dimethyl-2,5-diaminobenzene, 1,4-diamino isopropyl benzene and/or 1-amino-4-β-hydroxypropyl aminobenzene, pyrazole and the derivatives thereof such as 1-hydroxyethyl-4,5-diaminopyrazole, 3,4-diamino-5-hydroxypyrazole, 3,5-diaminopyrazole, 3,5-diamino pyrazol-1-carboxamide, 3-amino-5-hydroxypyrazole, 1-phenyl-2-methylpyrazole, 1-phenyl-3-methylpyrazole-5-one, 3,5-dimethylpyrazole, 3,5-dimethylpyrazole-1-methanol, 3,5-diamino-1,2,4-triazole, 4-aminophenol and the derivatives thereof such as 4-amino-3-methylphenol, 2-chloro-4-aminophenol, 2,6-dichloro-4-aminophenol, 2,4-diamino-phenol, 2,6-dibromo-4-aminophenol, tetramino pyrimidines, triaminohydroxy pyrimidines, diaminomono- and -dihydroxy pyrimidines, aminotriazines, 5-amino salicylic acid and 1,2,4-triamino benzene, or the water-soluble salts thereof.

Preferably, at least one oxidative dyestuff precursor is selected from p-phenylenediamines, and substituted p-phenylenediamines such as 2,5-diamino-toluene, 2-(2,5-diaminophenyl)ethanol, 1-amino-4-bis-(2'-hydroxy-ethyl)aminobenzene, p-aminophenols such as p-methylaminophenol, pyrazols such as 1-hydroxyethyl-4,5-diaminopyrazole, pyrimidines such as tetramino pyrimidines, triaminohydroxy pyrimidines, and indols and indolines such as 6-hydroxyindole, 5,6-dihydroxyindole, 5,6-dihydroxyindoline and their respective salts.

More preferably at least one oxidative dye precursor is selected from p-phenylenediamine, 2,5-diamino-toluene, 2-(2,5-diaminophenyl)ethanol, 1-amino-4-bis-(2'-hydroxyethyl)amino-benzene, p-aminophenol, p-methylaminophenol, 1-hydroxyethyl-4,5-diaminopyrazole and their respective salts.

Total concentration of oxidative dye precursors are in the range of 0.01 to 10% by weight, preferably 0.05 to 7.5% by weight and more preferably 0.1 to 5% by weight, calculated to total composition prior to mixing with an oxidizing agent.

The composition according to the invention preferably comprises one or more additional coupling substance. Suitable ones are resorcinol, 2-methyl resorcinol, 4-chlororesorcinol, 2-amino-4-chlorophenol, 5-amino-4-methoxy-2-methylphenol, 3-amino-phenol, 1-methyl-2-hydroxy-4-aminobenzene, 3-N,N-dimethyl aminophenol, 2.6-dihydroxy-3.5-dimethoxypyridine, 5-amino-3-methylphenol, 6-amino-3-methylphenol, 3-amino-2-methylamino-6-methoxypyridine, 2-amino-3-hydroxypyridine, 2-dimethyl-amino-5-aminopyridine, 2,6-diaminopyridine, 5-amino-2-methylphenol, 2-methyl-5-hydroxyethylaminophenol, 2-methyl-5-amino-6-chlorphenol, 2-bis(2-hydroxyethyl)aminotoluene, 2-amino-5-methylphenol,α-naphthol, 4,6-dichlororesorcinol, 1-hydroxy naphthalene, 4-hydroxy-1,2-methylenedioxy benzene, 1,5-dihydroxy naphthalene, 1,6-dihydroxy naphthalene, 1,7-dihydroxy naphthalene, 2,7-dihydroxy naphthalene, 1-hydroxy-2-methyl naphthalene, 4-hydroxy-1.2-methyldioxybenzene, 5-amino-2-methoxyphenol, hydroxybenzomorpholine, 1,2,4-trihydroxybenzene, phenylmethylpyrazolone, 3-amino-2,4-dichlorophenol, hydroxyethyl-3,4-methylenedioxyaniline, 2.6-dimethoxy-3,5-dimethylpyridine, 5-amino-4-chloro-2-methylphenol, hydroxypropyl-bis-(N-hydroxyethyl-p-phenylenediamine), 1-acetoxy-2-methylnaphthalene, 2,2'-methylenebis-4-aminophenol, 1,3-bis(2,4-diaminophenoxy)propane and/or their respective salts.

Preferably one or more couplers are selected from resorcinol, 2-methyl resorcinol, 4-chlororesorcinol, 3-amino-phenol, 1-methyl-2-hydroxy-4-aminobenzene, 2.6-dihydroxy-3,4-dimethylpyridine, 4-amino-3-methylphenol, 6-amino-3-methylphenol, 3-amino-2-methylamino-6-methoxypyridine, 2-amino-3-hydroxypyridine, 2-methyl-5-hydroxyethylaminophenol, 2-methyl-5-amino-6-chlorphenol, α-naphthol, 1,5-dihydroxy naphthalene, 2,7-dihydroxy naphthalene, 1-hydroxy-2-methyl naphthalene, hydroxybenzomorpholine, 1,2,4-trihydroxybenzene, phenylmethylpyrazolone, 3-amino-2,4-dichlorophenol, hydroxyethyl-3,4-methylenedioxyaniline, 2.6-dimethoxy-3,5-dimethylpyridine, 5-Amino-4-chloro-2-methylphenol, hydroxypropyl-bis-(N-hydroxyethyl-p-phenylenediamine), 1-acetoxy-2-methylnaphthalene, 2,2'-methylenebis-4-aminophenol, 1,3-bis(2,4-diaminophenoxy)propane and/or their respective salts.

More preferably, one or more additional couplers are selected from resorcinols such as resorcinol, 2-methyl resorcinol, 4-chlororesorcinol and/or m-aminophenols such as 3-amino-phenol, 1-methyl-2-hydroxy-4-aminobenzene, 2-methyl-5-hydroxyethylaminophenol, 2-methyl-5-amino-6-chlorphenol, 1,3-bis(2,4-diaminophenoxy)propane and/or their respective salts.

Total concentration of one or more coupling substances and their salts is in the range of 0.01 to 5% by weight, preferably 0.05 to 3% by weight and more preferably 0.1 to 2.5% by weight, calculated to total composition prior to mixing with an oxidizing agent.

Composition of the present invention comprises one or more direct dyes as an additional hair dye. Direct dyes suitable are selected from cationic dyes, anionic dyes and/or nitro dyes.

Suitable non-limiting examples to cationic ones are Basic Blue 6, Basic Blue 7, Basic Blue 9, Basic Blue 26, Basic Blue 41, Basic Blue 99, Basic Brown 4, Basic Brown 16, Basic Brown 17, Natural Brown 7, Basic Green, Basic Orange 31, 1, Basic Red 2, Basic Red 12 Basic Red 22, Basic Red 76 Basic Red 51, Basic Violet 1, Basic Violet 2, Basic Violet 3, Basic Violet 10, Basic Violet 14, Basic Yellow 57 and Basic Yellow 87.

Suitable non-limiting examples to anionic ones are Acid Black 1, Acid Blue 1, Acid Blue 3, Food Blue 5, Acid Blue 7, Acid Blue 9, Acid Blue 74, Acid Orange 3, Acid Orange 6, Acid Orange 7, Acid Orange 10, Acid Red 1, Acid Red 14, Acid Red 18, Acid Red 27, Acid Red 50, Acid Red 52, Acid Red 73, Acid Red 87, Acid Red 88, Acid Red 92, Acid Red 155, Acid Red 180, Acid Violet 9, Acid Violet 43, Acid Violet 49, Acid Yellow 1, Acid Yellow 23, Acid Yellow 3, Food Yellow No. 8, D&C Brown No. 1, D&C Green No. 5, D&C Green No. 8, D&C Orange No. 4, D&C Orange No. 10, D&C Orange No. 11, D&C Red No. 21, D&C Red No. 27, D&C Red No. 33, D&C Violet 2, D&C Yellow No. 7, D&C Yellow No. 8, D&C Yellow No. 10, FD&C Red 2, FD&C Red 40, FD&C Red No. 4, FD&C Yellow No. 6, FD&C Blue 1, Food Black 1, Food Black 2, Disperse Black 9 and Disperse Violet 1 and their alkali metal salts such as sodium, potassium.

Suitable non-limiting examples to nitro dyes are HC Blue No. 2, HC Blue No. 4, HC Blue No. 5, HC Blue No. 6, HC Blue No. 7, HC Blue No. 8, HC Blue No. 9, HC Blue No. 10, HC Blue No. 11, HC Blue No. 12, HC Blue No. 13, HC Blue No. 17, HC Brown No. 1, HC Brown No. 2, HC Green No. 1, HC Orange No. 1, HC Orange No. 2, HC Orange No. 3, HC Orange No. 5, HC Red BN, HC Red No. 1, HC Red No. 3, HC Red No. 7, HC Red No. 8, HC Red No. 9, HC Red No. 10, HC Red No. 11, HC Red No. 13, HC Red No. 54, HC Red No. 14, HC Violet BS, HC Violet No. 1, HC Violet No. 2, HC Yellow No. 2, HC Yellow No. 4, HC Yellow No. 5, HC Yellow No. 6, HC Yellow No. 7, HC Yellow No. 8, HC Yellow No. 9, HC Yellow No. 10, HC Yellow No. 11, HC Yellow No. 12, HC Yellow No. 13, HC Yellow No. 14, HC Yellow No. 15, 2-Amino-6-chloro-4-nitrophenol, picramic acid, 1,2-Diamino-4-nitrobenzol, 1,4-Diamino-2-nitrobenzol, 3-Nitro-4-aminophenol, 1-Hydroxy-2-amino-3-nitrobenzol and 2-hydroxyethylpicramic acid.

Preferred direct dyes are cationic dyes such as Basic Red 51, Basic Orange 31, Basic Yellow 57 and Basic Yellow 87, anionic dyes such as Acid Yellow 1, Acid Yellow 23, Acid Yellow 3, D&C Orange No. 4, and Disperse Black 9 and nitro dyes such as HC Orange No. 1, HC Orange No. 2, Yellow No. 2, HC Yellow No. 4, HC Yellow No. 7, HC Yellow No. 9, HC Yellow No. 10, HC Yellow No. 13, picramic acid, 3-Nitro-4-aminophenol, 2-hydroxyethylpicramic acid, 3-Methylamino-4-nitrophenoxyethanol, 2-Nitro-5-glycerylmethylaniline, 4-Nitrophenyl aminoethylurea, Hydroxy-2-nitro-p-toluidine, and 2-Chloro-6-ethylamino-4-nitrophenol, and their respective salts.

More preferred direct dyes are cationic dyes such as Basic Red 51, Basic Orange 31, Basic Yellow 57 and Basic Yellow 87 and nitro dyes such as HC Orange No. 1, HC Orange No. 2, Yellow No. 2, HC Yellow No. 4, HC Yellow No. 7, HC Yellow No. 9, HC Yellow No. 10, HC Yellow No. 13, picramic acid, 3-Nitro-4-aminophenol, 2-hydroxyethylpicramic acid, 3-Methylamino-4-nitrophenoxyethanol, 2-Nitro-5-glycerylmethylaniline, 4-Nitrophenyl aminoethylurea, Hydroxy-2-nitro-p-toluidine, and 2-Chloro-6-ethylamino-4-nitrophenol, and their respective salts.

Most preferred are nitro dyes and especially those of HC Orange No. 1, HC Orange No. 2, Yellow No. 2, HC Yellow No. 4, HC Yellow No. 7, HC Yellow No. 9, HC Yellow No. 10, HC Yellow No. 13, picramic acid, 3-Nitro-4-aminophenol, 2-hydroxyethylpicramic acid, 3-Methylamino-4-nitrophenoxyethanol, 2-Nitro-5-glycerylmethylaniline, 4-Nitrophenyl aminoethylurea, Hydroxy-2-nitro-p-toluidine, and 2-Chloro-6-ethylamino-4-nitrophenol, and their respective salts.

Total concentration of one or more direct dyes is in the range of 0.001 to 10%, preferably 0.001 to 7.5%, more preferably 0.01 to 5% by weight calculated to total composition prior to mixing with oxidizing agent.

pH of the composition of part A is alkaline and preferably in the range of 8 to 12, more preferably 9 to 10.5 and most preferably 9 to 10.

Part B of the composition comprises at least one oxidizing agent. Suitable oxidizing agents are urea peroxide, melamine peroxide and hydrogen peroxide. Preferred is hydrogen peroxide. Oxidizing agent is comprised at a concentration of 0.1 to 20% by weight and preferably 1 to 15% by weight calculated to total of the composition B.

pH of the composition of Part B is acidic and in the range of 1 to 6, preferably 2 to 5 and more preferably 2 to 4.

pH of the composition obtained after mixing parts A and B is in the range of 5 to 12, preferably 6 to 11 and more preferably 6.8 to 10.

Part A and B are mixed at a weight ratio of 3:1 to 1:3, preferably 2:1 to 1:2.

Composition of the present invention is preferably an aqueous and comprises at least 40% by weight water calculated to total of the composition, after mixing parts A and B.

Composition of the present invention can comprise additionally substances customarily found in colouring compositions.

Compositions of the present invention can be in the form of solutions, dispersions, gels and emulsions. Most preferred is emulsion.

Coloring composition of present invention can comprise additionally in the base formulation fatty acids with 0 to 3 ethylenic bonds and with fatty acyl chain length of 12 to 22 C atom. Concentration of the fatty acids can be in the range of 0.1 to 10%, preferably 0.1 to 7.5% and most preferably 0.2 to 5% by weight calculated to the total composition, prior to mixing with oxidizing agent. Non-limiting examples are myristic acid, palmitic acid, behenic acid, steraic acid, oleic acid, linoleic acid. The most preferred fatty acid is oleic acid.

Coloring composition of the present invention comprise at least one fatty alcohol or mixture of fatty alcohols with the chain length of 14 to 22 C atoms which may be straight or branched, saturated or unsaturated. Examples to suitable fatty alcohols, without limiting the choice, are myristyl alcohol, cetyl alcohol, stearyl alcohol, behenyl alcohol, oleyl alcohol and cetostearyl alcohol, octyldodecanol.

The most preferred is cetostearyl alcohol well known with its trade name Lanette O or as Lanette N in mixture with sodium cetearyl sulfate from Cognis. Total fatty alcohol content should be in the range of 1 to 20% by weight, calculated to total composition prior to mixing with an oxidizing agent.

Colouring compositions according to present invention comprises surfactants selected from anionic, amphoteric (or zwiterionic) and/or cationic surfactants as emulsifier or solubilizer. Cationic surfactants are as well used as hair conditioners in the colouring composition.

The preferred non-ionic emulsifiers are ethoxylated fatty alcohols with an alkyl chain of 12 to 24 C atoms and with number of ethoxyl groups of 2 to 50, preferably 10 to 30. Examples are ceteth-20, seteareth-30, palmeth-20, steareth-20, beheneth-20 etc. These compounds are named according to the fatty alcohol they are originating and number of ethoxyl groups is given at the end. These compounds are well known emulsifiers and found in any cosmetic ingredient book.

Further suited nonionic surfactants are, especially in mixture with fatty alcohol ethoxylates, for example, long-chain fatty acid mono- and dialkanolamides, such as coco fatty acid mono- or diethanolamide and myristic fatty acid mono or diethanolamide, stearic acid mono or diethanolamide.

Further nonionic surfactants suited again especially in admixture with fatty alcohol ethoxylates mentioned above are alkyl polyglucosides of the general formula $$R_6-O-(R_3O)_n-Z_x,$$

wherein $R_6$ is an alkyl group with 8 to 18 carbon atoms, $R_3$ is an ethylene or propylene group, Z is a saccharide group with 5 to 6 carbon atoms, n is a number from 0 to 10 and x is a number between 1 and 5.

Further additionally useful nonionic surfactants are, for example, the various sorbitan esters, such as polyethylene glycol sorbitan stearic acid ester, fatty acid polyglycol esters or poly-condensates of ethyleneoxide and propyleneoxide, as they are on the market, for example, under the trade name "Pluronics®", as well as fatty alcohol ethoxylates.

Further suitable nonionic surfactants are amineoxides. Such amineoxides are state of the art, for example $C_{12}$-$C_{18}$-alkyl dimethyl amineoxides such as lauryl dimethyl amineoxide, $C_{12}$-$C_{18}$-alkyl amidopropyl or -ethyl amineoxides, $C_{12}$-$C_{18}$-alkyl di(hydroxyethyl) or (hydroxypropyl) amineoxides, or also amineoxides with ethyleneoxide and/or propyleneoxide groups in the alkyl chain. Such amineoxides are on the market, for example, under the trade names "Ammony®", "Aromox®" or "Genaminox®".

Anionic surfactants suitable within the scope of the invention are in principal known from the cleansing compositions and may be present in an amount from 0.1 to about 10% by weight, calculated to the total composition prior to mixing with an oxidizing agent. Compatibility of anionic surfactant in the composition should be taken into account when choosing the type and the concentration.

These are anionic surfactants of the sulfate, sulfonate, carboxylate and alkyl phosphate type, for example, the known $C_{10}$-$C_{18}$-alkyl sulfates, and in particular the respective ether sulfates, for example, $C_{12}$-$C_{14}$-alkyl ether sulfate, lauryl ether sulfate, especially with 1 to 4 ethylene oxide groups in the molecule, monoglyceride (ether) sulfates, fatty acid amide sulfates obtained by ethoxylation and subsequent sulfatation of fatty acid alkanolamides, and the alkali salts thereof, as well as the salts of long-chain mono- and dialkyl phosphates.

Additional anionic surfactants useful within the scope of the invention are α-olefin sulfonates or the salts thereof, and in particular alkali salts of sulfosuccinic acid semiesters, for example, the disodium salt of monooctyl sulfosuccinate and alkali salts of long-chain monoalkyl ethoxysulfosuccinates.

Suitable surfactants of the carboxylate type are alkyl polyether carboxylic acids and the salts thereof of the formula $$R_5(C_2H_4O)_n-O-CH_2COOX,$$

wherein $R_5$ is a $C_8$-$C_{20}$-alkyl group, preferably a $C_{12}$-$C_{14}$-alkyl group, n is a number from 1 to 20, preferably 2 to 17, and X is H or preferably a cation of the group sodium, potassium, magnesium and ammonium, which can optionally be hydroxyalkyl-substituted, as well as alkyl amido polyether carboxylic acids of the general formula $$R_5-\underset{\underset{O}{\|}}{C}-\underset{\underset{H}{|}}{N}-CH_2-CH_2-(C_2H_4O)_n-CH_2COOX$$

wherein $R_5$ and X have the above meanings, and n is in particular a number from 1 to 10, preferably 2.5 to 5.

Such products have been known for some time and are on the market, for example, under the trade name "AKYPO®" and "AKYPO-SOFT®".

Also useful are $C_8$-$C_{20}$-acyl isethionates, alone or in admixture with other anionic surfactants, as well as sulfofatty acids and the esters thereof.

Further suitable anionic surfactants are also $C_8$-$C_{22}$-acyl aminocarboxylic acids or the water-soluble salts thereof. Especially preferred is N-lauroyl glutamate, in particular as sodium salt, as well as, for example, N-lauroyl sarcosinate, N—$C_{12}$-$C_{18}$-acyl asparaginic acid, N-myristoyl sarcosinate, N-oleoyl sarcosinate, N-lauroyl methylalanine, N-lauroyl lysine and N-lauroyl aminopropyl glycine, preferably in form of the water-soluble alkali or ammonium, in particular the sodium salts thereof, preferably in admixture with the above-named anionic surfactants.

It is also possible to use mixtures of several anionic surfactants.

An overview of the anionic surfactants suitable for the present invention can furthermore be found in the monography of K. Schrader, "Grundlagen and Rezepturen der Kosmetika", $2^{nd}$ Ed. (1989, Hüthig Buchverlag), pp. 595-600 and pp. 683 to 691.

As further surfactant component, the colouring compositions according to the invention can also contain amphoteric or zwitterionic surfactants, for example in an amount from about 0.5% to about 5%, preferably from about 1% to about 2.5% by weight, calculated to the total composition.

Useful as such are in particular the various known betaines such as alkyl betaines, fatty acid amidoalkyl betaines and sulfobetaines, for example, lauryl hydroxysulfobetaine; long-chain alkyl amino acids, such as cocoaminoacetate, cocoaminopropionate and sodium cocoamphopropionate and -acetate have also proven suitable.

Colouring composition can comprise cationic surfactants as emulsifier, solubilizer and/or conditioning ingredients according to the formula, $$R_8-\underset{\underset{R_{11}}{|}}{\overset{\overset{R_9}{|}}{N^+}}-R_{10}\quad X^-$$

where $R_8$ is a saturated or unsaturated, branched or non-branched alkyl chain with 8-22 C atoms or $$R_{12}CO\,NH(CH_2)_n$$

where $R_{12}$ is saturated or unsaturated, branched or non-branched alkyl chain with 7-21 C atoms and n has typical value of 1-4 or $$R_{13}CO\,O(CH_2)_n$$

where $R_{13}$ is saturated or unsaturated, branched or non-branched alkyl chain with 7-21 C atoms and n has typical value of 1-4, and $R_9$ is unsaturated or saturated, branched or non-branched alkyl chain with 1-22 C atoms or $R_{12}CO\,NH(CH_2)_n$ or $R_{13}CO\,O(CH_2)_n$ where $R_{12}$, $R_{13}$ and n are same as above.

$R_{10}$ and $R_{11}$ are lower alkyl chain with 1 to 4 Carbon atoms, and X is typically chloride, bromide, methosulfate.

Typical examples of those ingredients are cetyl trimethly ammonium chloride, stear trimonium chloride, dipalmitoyl dimonium chloride, distearyl dimethyl ammonium chloride, stearamidopropyl trimonuim chloride, dioleoylethyl dimethyl ammonium methosulfate, dioleoylethyl hydroxyethylmonium methosulfate.

Form the above mentioned surfactants preferred are non-ionic and anionic surfactants and their mixtures.

Total surfactant concentration is in the range of 0.5 to 15%, preferably 1 to 10%, more preferably 1 to 7.5% by weight calculated to total composition prior to mixing with an oxidizing agent.

Colouring composition can also contain cationic polymers as conditioning agents. Those are cationic cellulose type polymers know as Polymer JR type from Amerchol such as Polyquaternium 10 or cationic guar gum known with trade name Jaguar from Rhône-Poulenc and chemically for example Guar hydroxypropyl trimonium chloride. Furthermore, chitosan and chitin can also be included in the compositions as cationic natural polymers.

Furthermore, it has been found suitable those cationic polymers known with their CTFA category name Polyquaternium. Typical examples of those Polyquaternium 2, Polyquaternium 4, Polyquaternium 6, Polyquaternium 7, Polyquaternium 10, Polyquaternium 11, Polyquaternium 16, Polyquaternium 22 and Polyquaternium 28, Polyquatemium 30, Polyquaternium 37, Polyquaternium 36, Polyquaternium 46, Polyquaternium 67, Polyquaternium 87.

Typical concentration range for any of the cationic conditioners mentioned above can be 0.01-5% by weight, preferably 0.03-2.5% by weight and more preferably 0.05-1.5% by weight.

Hair dyeing composition of the present invention preferably comprise an organopolysiloxane wherein at least one silicium atom is linked to an alkylene group having a heteroatom, in particular a nitrogen atom, with a poly-(N-acyl alkyleneimine) units of the formula

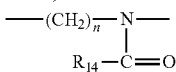

wherein n is a number from 1 to 5 and $R_{14}$ is hydrogen, a $C_1$-$C_{12}$-alkyl or cycloalkyl, aralkyl or aryl group.

Preferred organopolysiloxane polymers are those of the type disclosed in EP-A 640 643, in particular optionally quaternized aminoalkyl, in particular aminopropyl dimethyl polysiloxane/polyethyl oxazoline copolymers of the formula

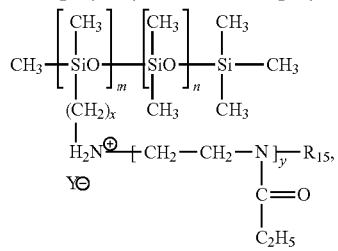

wherein m and n each are numbers from 20 to 10,000, in particular 50 to 7,000, especially 100 to 5,000, x is a number between 1 and 5, preferably 3, and y is a number from 5 to 30, $R_{15}$ is a $C_1$-$C_{12}$-alkyl or aryl group, in particular a methyl, ethyl or benzyl group, and $Y^-$ is an anion.

Especially suited are the organopolysiloxanes disclosed under the terms A-1, A-2 and A-3 on pages 12 to 13 of EP-A 640 643. The proportion of graft copolymers in the hair colouring compositions according to the invention ranges from 0.05% to 5%, preferably 0.1% to 2.5%, in particular 0.5% to 1.5% by weight, calculated to the total composition.

Coloring compositions according to the present invention can contain organic solvents as penetration enhancers and also as a solubilzers. Examples of such organic solvents are benzyloxy ethanol, benzyl alcohol, phenoxy ethanol, phenoxy isopropanol, methyl phenoxy ethanol, benzyl glycerol, N-benzyl formide, N-methylpyrrolidone, N-ethyl pyrrolidone, cinnamyl alcohol, phenethyl alcohol, p-methyl benzyl alcohol, butyl cellosolve, methyl carbitol, ethyl carbitol, propyl carbitol, butyl carbitol, diethyleneglycol, diethyl ether and dipropyleneglycol diethyl ether. Typically the concentration of those solvents can be in the range from 0.5% to 20%, preferably 0.5-15%, more preferably 0.5-10%, by weight calculated to the total composition, prior to mixing with oxidizing composition.

Colouring compositions according to the invention may comprise thickening agents. These are, for example, the various cellulose derivatives such as hydroxyalkyl celluloses, e.g. hydroxyethyl cellulose, hydroxypropyl cellulose, hydroxypropyl methyl cellulose, natural polysaccharides such as xanthan gum; guar gum and the alkoxylation products thereof in amounts from 0.1-5%, preferably 0.1-3% and most preferably 0.1-2% by weight calculated to the total composition prior to mixing with oxidizing composition and depending on the desired consistency thereof.

Optionally, the colouring composition of this invention can comprise further hair conditioning agents such as silicone oils either volatile or non-volatile, natural and synthetic oils. Among silicone oils those can be added to the colouring composition include dimethicone, dimethiconol, polydimethylsiloxane, DC fluid ranges from Dow Corning, natural oils such as olive oil, almond oil, avocado oil, weizenkeim oil, ricinus oil and the synthetic oils, such as mineral oil, isopropyl-myristate, palmitate, stearate and isostearate, oleyl oleate, isocetyl stearate, hexyl laurate, dibutyl adipate, dioctyl adipate, myristyl myristate and oleyl erucate.

Additional non-ionic conditioning agents may be polyols such as glycerin, glycol and derivatives, polyethyleneglycoles known with trade names Carbowax PEG from Union Carbide and Polyox WSR range from Amerchol, polyglycerin and polyethyleneglycol mono or di fatty acid esters.

Compositions may further comprise at least one ubiquinone of the formula

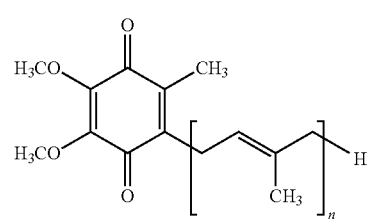

where n is a number between 1 and 10 at a concentration of 0.0001 to 1%, preferably from 0.0002 to 0.75%, more preferably from 0.0002 to 0.5% and most preferably from 0.0005 to 0.5% by weight, calculated to total composition, prior to mixing with oxidizing composition.

The composition comprises ubiquinone which is preferably selected from the ones where n is a number between 6 and 10 and more preferably it is ubiquinone 50 where n is 10, also known as Coenzyme Q10.

Composition can comprise at least one amino acid. At least one amino acid is comprised at a concentration of 0.01 to 10%, preferably 0.05 to 7.5% and more preferably 0.1 to 5% and most preferably 0.25 to 5% by weight calculated to total of each composition, prior to mixing with oxidizing composition.

Suitable amino acids are glycin, histidine, citrullin, asparagine, alanin, valin, leucin, isoleucin, pyrrolin, tryptophane, phenylalanine, methionine, serine, tyrosine, threonine and gluatamine. Preferably, the amino acid is selected from glycin, histidine, citrullin, asparagine, alanin, valin, leucin, isoleucin, pyrrolin, serine, tyrosine, threonine and gluatamine. More preferably, at least one amino acid is selected from glycin, histidine, asparagine, alanin, valin, leucin, pyrrolin, serine, tyrosine and gluatamine, and most preferably at least one amino acid is selected from glycin, asparagine, alanin, valin, leucin, and serine.

Composition can comprise further ceramide type of compound with the general formula

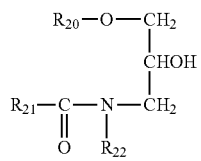

where $R_{20}$ and $R_{21}$ are independent from each other alkyl- or alkenyl group with 10 to 22 carbon atoms, $R_{22}$ is alkyl or hydroxyl alkyl with 1 to 4 carbon atoms group and n is a number between 1 to 6, preferably 2 or 3. Preferred compound according to the above chemical structure is cetyl-PG-hydroxyethylpalmitamide.

Further optional ingredient are sterols, especially the phytosterols as preferred hair restructuring agents. Especially preferred ones are of plant origin for example ergosterol, sitosterol, stigmasterol, fucosterol, brassicasterol, fungisterol, campesterol, zymosterol, ascosterol, cerevisterol, episterol, faecosterol, spinasterol. Among those phytosterols, the ones found in "Avocadin" which is the unsaponified fraction of the avocado oil is more preferred.

Additionally, one or more natural oil may be incorporated into the compositions of the present invention. Suitable are such as olive oil, almond oil, avocado oil, wheatgerm oil, ricinus oil or their mixture. Concentration of natural oil should be 0.01 to 2.5%, preferably 0.01. to 1%, more preferably 0.05 to 0.5% by weight, calculated to total each composition, prior to mixing with oxidizing composition.

Furthermore, composition of the present invention is suitably provided to the users in the form of a kit. Accordingly, further object of the present invention is a kit comprising at least two compositions Parts A and B wherein Part A comprises at least one cationic antraquinone dye and at least one at least one additional dyestuff selected from direct and oxidative dyes and part B has an acidic pH and comprises at least one oxidizing agent.

Compositions of the present invention can further comprise ingredients customarily found in such compositions such as alkalizing agents, preservatives antioxidants, fragrances, reducing agents and chelating agents.

The following examples are to illustrate the present invention, but not to limit.

EXAMPLE 1

| Base composition | |
|---|---|
| | % by weight |
| Octyldodecanol | 1.3 |
| Cetearyl alcohol | 1.0 |
| Oleyl alcohol | 2.6 |
| Ceteareth-20 | 1.0 |
| Sodium lauryl sulphate | 1.0 |
| Xanthan gum | 1.0 |
| Sodium sulfit | 0.5 |
| Ascorbic acid | 0.2 |
| Tetrasodium EDTA | 0.2 |
| Fragrance, preservative | q.s |
| Ammonia 25% | 8.0 |
| Water | q.s. to 100 |

| | Compositions | | | | | | | | | |
|---|---|---|---|---|---|---|---|---|---|---|
| Dyestuffs | I | II | III | IV | V | VI | VII | VIII | IX | X |
| Structure 1a | | | | 0.5 | 0.5 | 0.5 | 0.5 | 0.5 | 0.5 | 0.5 |
| Structure 1b | 0.5 | 0.5 | | | | | | | | |
| Structure 1s | | | 0.5 | | | | | | | |
| p-Toluenediamine | | | | 0.5 | | | 0.5 | | | |
| p-Phenylenediamine | | | | | 0.5 | | | | | |
| p-Aminophenol | 0.3 | | 0.3 | | | 1.0 | | | | |
| m-Aminophenol | | 0.3 | | 0.3 | | 0.3 | 0.1 | | | |
| 4-Amino-2-hydroxytoluene | | | | | 0.3 | 0.4 | 0.1 | | | |
| Resorcinol | 0.2 | | 0.2 | 0.2 | | | 0.2 | | | |
| 2-amino-3-hydroxytoluene | | 0.1 | | | 0.1 | | 0.1 | | | |
| Sodium Picramate | | | | | | | 0.05 | | | 0.2 |
| HC Yellow 2 | | | | | | | | | | 0.2 |
| 2-Amino-6-chloro-4-nitrophenol | | | | | | | 0.05 | | | 0.3 |
| Basic Red 51 | | | | | | | | 0.3 | | |
| Basic Yellow 87 | | | | | | | | 0.1 | | |

-continued

| Dyestuffs | I | II | III | IV | V | VI | VII | VIII | IX | X |
|---|---|---|---|---|---|---|---|---|---|---|
| HC Blue 17 | | | | | | | | | 0.3 | |
| Color | Brown | Brown | Brown | Cool Brown | Violet Brown | Violet | Ash Brown | Violet | Blue | Light Brown |

| Dyestuffs | XI | XII | XIII | XIV | XV | XVI | XVII | XVIII | XIX | XX |
|---|---|---|---|---|---|---|---|---|---|---|
| Structure 1m | | | | 0.5 | 0.5 | 0.5 | 0.5 | 0.5 | 0.5 | 0.5 |
| Structure 1t | 0.5 | 0.5 | | | | | | | | |
| Structure 1n | | | 0.5 | | | | | | | |
| p-Toluenediamine | | | | 0.5 | | | 0.5 | | | |
| p-Phenylenediamine | | | | | 0.5 | | | | | |
| p-Aminophenol | 0.3 | | 0.3 | | | 1.0 | | | | |
| m-Aminophenol | | 0.3 | | 0.3 | | 0.3 | 0.1 | | | |
| 4-Amino-2-hydroxytoluene | | | | | 0.3 | 0.4 | 0.1 | | | |
| Resorcinol | 0.2 | | 0.2 | 0.2 | | | 0.2 | | | |
| 2-amino-3-hydroxytoluene | | 0.1 | | | 0.1 | | 0.1 | | | |
| Sodium Picramate | | | | | | | | 0.05 | | 0.2 |
| HC Yellow 2 | | | | | | | | | | 0.2 |
| 2-Amino-6-chloro-4-nitrophenol | | | | | | | | 0.05 | | 0.3 |
| Basic Red 51 | | | | | | | | 0.3 | | |
| Basic Yellow 87 | | | | | | | | 0.1 | | |
| HC Blue 17 | | | | | | | | | 0.3 | |
| Color | Brown | Brown | Brown | Cool Brown | Violet Brown | Violet | Ash Brown | Violet | Blue | Light Brown |

The above compositions were mixed with a composition comprising 6% hydrogen peroxide at a weight ratio of 1:1 and applied onto hair and rinsed off from hair after processing of 30 min at ambient temperature. It was observed that hair was coloured homogeneously. The colours obtained are given below of each example.

The invention claimed is:

1. A dyeing composition for keratin fibres resulting from mixing of Part A and Part B wherein Part A has an alkaline pH and comprises at least one cationic antraquinone dye selected from the group consisting of

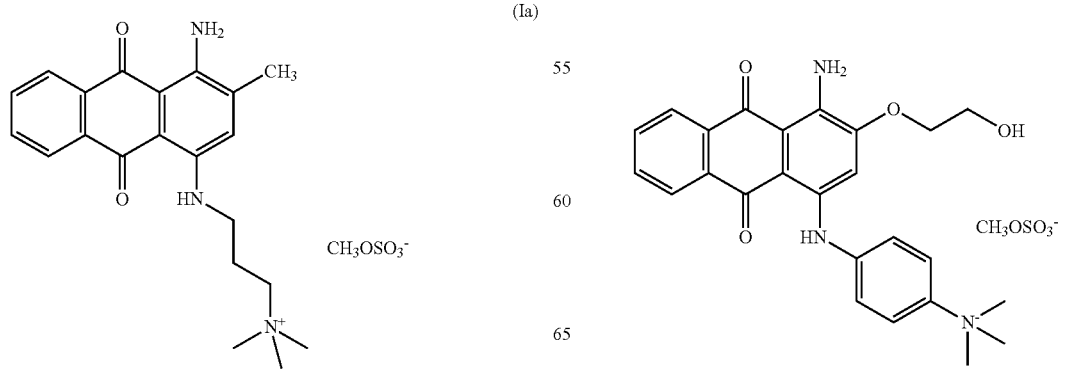

-continued

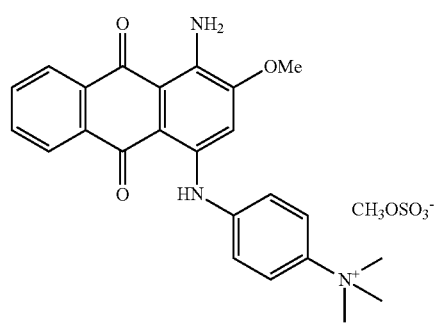

-continued
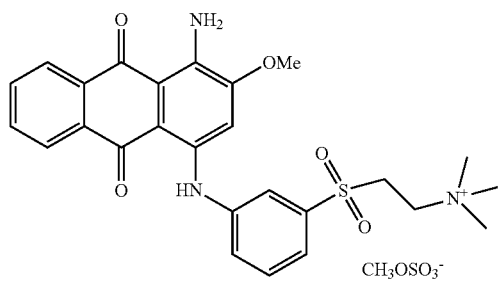
(Ie)
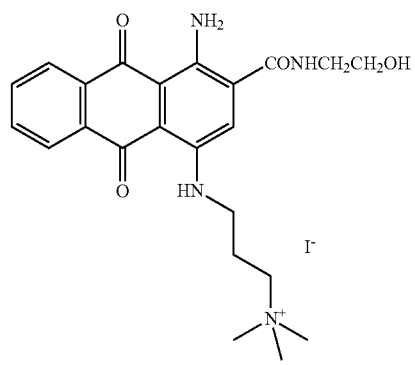
(Ir)
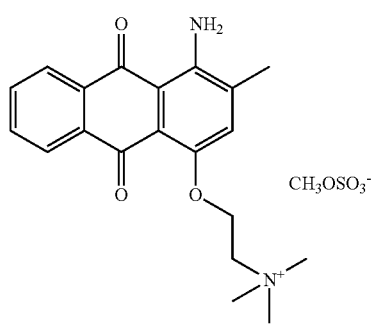
(If)
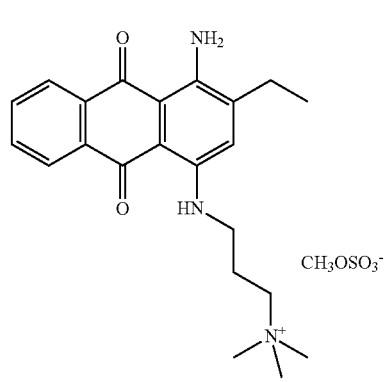
(Is)
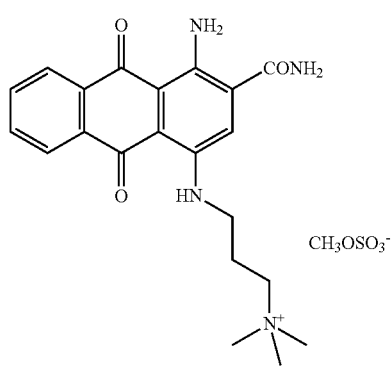
(Ig)
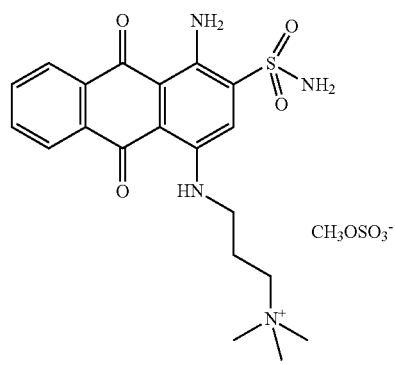
(Ix)
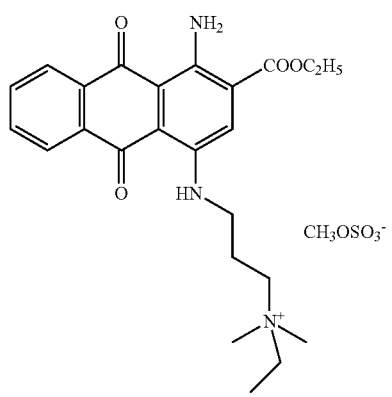
(Ih)
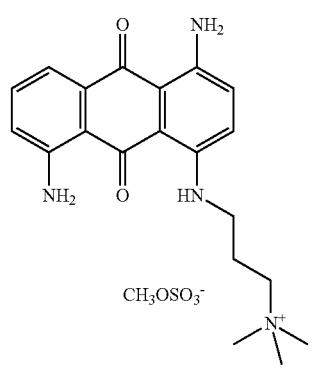
(Ij)

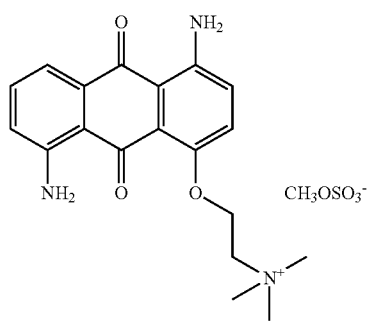 (Ik)
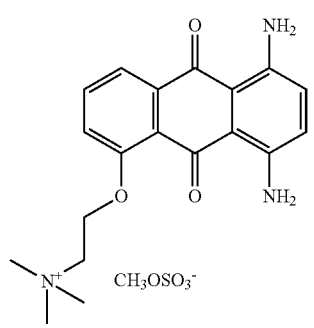 (Il)
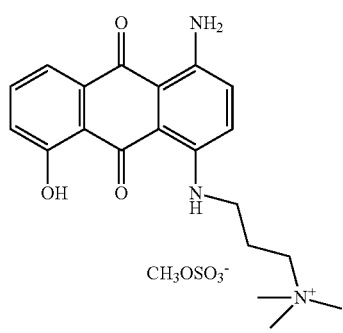 (Im)
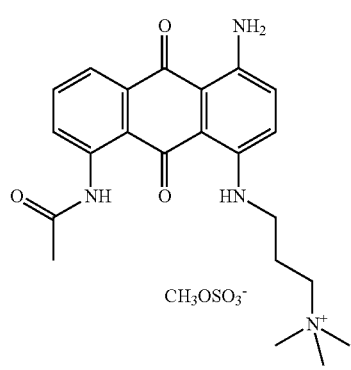 (In)
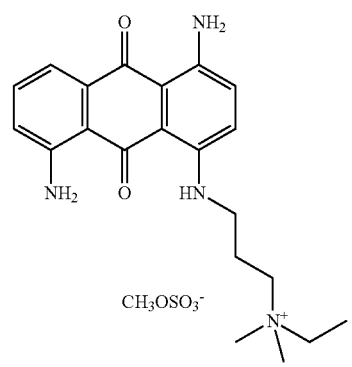 (It)
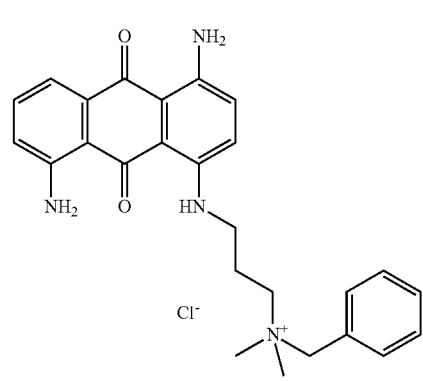 (Iu)
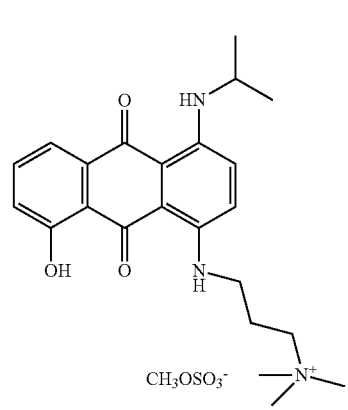 (Iy)
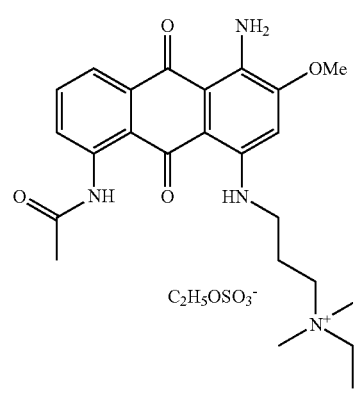 (Iv)

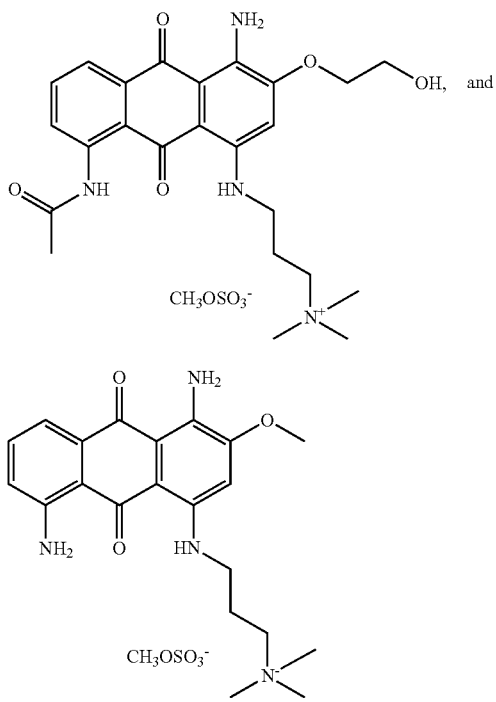

and at least one additional dyestuff selected from direct and oxidative dyes and Part B has an acidic pH and comprises at least one oxidizing agent, wherein Part A of the dyeing composition is an emulsion composition and comprises at least one fatty alcohol and at least one surfactant, wherein the at least one fatty alcohol is present at a concentration of 1 to 20% by weight calculated to total composition, prior to mixing with Part B, and further wherein the at least one surfactant is present at a concentration of 0.5 to 15% by weight calculated to a total composition, prior to mixing with Part B.

2. The composition according to claim 1 wherein the at least one cationic antraquinone dye is

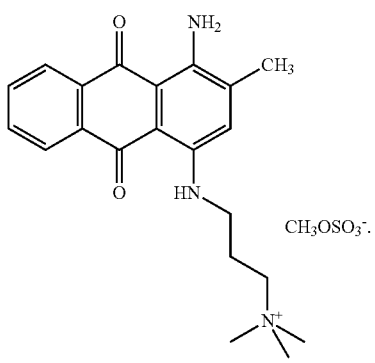

3. The composition according to claim 1, wherein the at least one cationic antraquinone dye is present at a concentration of 0.0001 to 10% by weight calculated to total of the composition, prior to mixing with Part B.

4. The composition according to claim 1, wherein the at least one additional dyestuff is selected from oxidative dyes precursors.

5. The composition according to claim 1, wherein the at least one additional dyestuff selected from cationic, anionic and neutral direct dyes.

6. The composition according to claim 1, wherein the at least one additional dyestuff is a direct dye selected from the group consisting of Basic Red 51, Basic Orange 31, Basic Yellow 57, Basic Yellow 87, Acid Yellow 1, Acid Yellow 23, Acid Yellow 3, D&C Orange No. 4, Disperse Black 9, HC Orange No. 1, HC Orange No. 2, Yellow No. 2, HC Yellow No. 4, HC Yellow No. 7, HC Yellow No. 9, HC Yellow No. 10, HC Yellow No. 13, picramic acid, 3-Nitro-4-aminophenol, 2-hydroxyethylpicramic acid, 3-Methylamino-4-nitrophenoxyethanol, 2-Nitro-5-glycerylmethylaniline, 4-Nitrophenyl aminoethylurea, Hydroxy-2-nitro-p-toluidine, and 2-Chloro-6-ethylamino-4-nitrophenol, and their respective salts.

7. The composition according to claim 1, wherein Part B comprises hydrogen peroxide as an oxidizing agent.

8. The composition according to claim 1, wherein Part A has a pH between 8 and 12.

9. The composition according to claim 1, wherein Part B has a pH between 1 and 6.

10. The composition according to claim 1, wherein the pH of the composition resulting from mixing parts A and B is in the range of 5 to 12.

11. The composition according to claim 1, wherein the composition resulting from mixing parts A and B is an aqueous composition and comprises at least 40% by weight calculated to total composition, water.

12. The composition according to claim 1, wherein the composition comprises at least one thickening agent present at a concentration of 0.1 to 5% by weight calculated to total composition, prior to mixing with Part B.

13. The composition according to claim 12, wherein the at least one thickening agent is selected from the group consisting of hydroxyethyl cellulose, hydroxypropyl cellulose, hydroxypropyl methyl cellulose, xanthan gum, guar gum and alkoxylation products thereof.

14. A method for dyeing keratin fibers, the method comprising:
applying the dyeing composition according to claim 1 to the keratin fibers for achieving long lasting homogeneous vibrant blue comprising colours.

15. A kit for colouring keratin fibres comprising at least two compositions, Parts A and B, wherein Part A is an alkaline composition and comprises at least one cationic antraquinone dyestuff and at least one at least one additional dyestuff selected from direct and oxidative dyes and Part B has an acidic pH and comprises at least one oxidizing agent, wherein Part A of the dyeing composition is an emulsion composition and comprises at least one fatty alcohol and at least one surfactant, wherein the at least one fatty alcohol is present at a concentration of 0.1 to 10% by weight calculated to total composition, prior to mixing with Part B, and further wherein the at least one surfactant is present at a concentration of 0.5 to 15% by weight calculated to a total composition, prior to mixing with Part B.

16. The composition according to claim 1, wherein the at least one fatty alcohol is selected from the group consisting of myristyl alcohol, cetyl alcohol, stearyl alcohol, behenyl alcohol, oleyl alcohol, cetostearyl alcohol, octyldodecanol and mixtures thereof.

17. The composition according to claim 16, wherein the concentration of the at least one surfactant is in a range from 1 to 10% by weight calculated to total composition, prior to mixing with Part B.

18. The composition according to claim 17, wherein the concentration of the at least one surfactant is in a range from 1 to 7.5% by weight calculated to total composition, prior to mixing with Part B.

\* \* \* \* \*